US006451560B1

(12) United States Patent
Harwood et al.

(10) Patent No.: US 6,451,560 B1
(45) Date of Patent: Sep. 17, 2002

(54) PROTEIN SECRETION

(76) Inventors: Colin R. Harwood, University of Newcastle upon Tyne Dept. of Microbiology, The Medical School Framlington Place, Newcastle upon Tyne NE2 4HH (GB); Keith Stephenson, The Scripps Research Institute Dept. of Molecular & Experimental Medicine 10550 No. Torrey Pines Rd., La Jolla, CA (US) 92037; Vesa Kontinen, National Public Health Institute Laboratory of Vaccine Development, Mannerheimintie 166, FIN-00300 Helsinki (FI); Matti Sarvas, National Public Health Institute Laboratory of Vaccine Development, Mannerheimintie 166, FIN-00300 Helsinki (FI)

( * ) Notice: Subject to any disclaimer, the term of this patent is extended or adjusted under 35 U.S.C. 154(b) by 0 days.

(21) Appl. No.: 09/743,279

(22) PCT Filed: Jul. 8, 1999

(86) PCT No.: PCT/GB99/02191

§ 371 (c)(1),
(2), (4) Date: Mar. 12, 2001

(87) PCT Pub. No.: WO00/03010

PCT Pub. Date: Jan. 20, 2000

(30) Foreign Application Priority Data

Jul. 8, 1998 (GB) ............................................. 9814672

(51) Int. Cl.[7] ................................................. C12P 21/02
(52) U.S. Cl. ...................................................... 435/69.1
(58) Field of Search ............................... 435/69.1, 252.3

(56) References Cited

PUBLICATIONS

Baltz et al., "Use of genomics and insertional mutagenesis to identify targets for antibiotic development in *Streptococcus pneumoniae*" (abstract), Interscience Conference on Antimicrobial Agents and Chemotherapy, vol. 37 (1997) p. 391.

O'Brian et al., "Correlation of teichoic acid D– alanyl esterification with the expression of methicillin resistance in *Staphylococcus aureus*", Microbios, (1995) pp. 119–137.

Peregro et al., "Incorporation of D–alanine into lipoteichoic acid and Wall Teichoic Acid in *Bacillus subtilis*", Journal of Biological Chemistry, vol. 270 No. 26, Jun. 30, 1995, pp. 15598–15606.

Peschel et al., "Inactivation of the dlt operon in *Staphylococcus aureus confers* sensitivity to defensins, protegrins, and other antimicrobial peptides", Journal of Biological Chemistry, vol. 274, No. 13, March 26, 1999, pp. 8405–8410.

Clemans et al., "Insertional inactivation of genes responsible for the D–alanylation of lipoteichoic acid in *Streptococcus gordonii* DL1 (Challis) affects intrageneric coaggregations", Infection and Immunity, May 1999, pp. 2464–2474.

Wecke et al., "D–alanine deprivation of *Bacillus subtilis* teichoic acids is without effect on cell growth and morphology but affects the autolytic activity", Microbial Drug Resistance, vol. 2, No. 1 (1996), pp. 123–129.

Wecke et al., "The absence of D–alanine from lipoteichoic acid and wall teichoic acid alters surface charge, enhances autolysis and increases susceptibility to methicillin in *Bacillus subtilis*", Microbiology, vol. 143, No. 9 (1997), pp. 2953–2960.

Kiriukhin et al., "Incorporation of D–alanine into the lipoteichoic acid of *Lactobacillus casei* 102S: Insertional inactivation of DltD", Abstracts of the General Meeting of the American Society for Microbiology, vol. 99 (1999), p. 424.

*Primary Examiner*—Terry McKelvey
(74) *Attorney, Agent, or Firm*—Crowell & Moring LLP (57) ABSTRACT

The invention relates to a novel prokaryotic expression system characterized by alterations to the dlt operon whereby expression of genes encoded therein may be regulated to limit the availability of polypeptides encoded by said genes.

18 Claims, 6 Drawing Sheets

PROTEIN SECRETION

The invention relates to a novel prokaryotic expression system and proteins expressed thereby.

The industrial production of proteins has, in many instances, exploited the native expression and secretory systems of microorganisms and specifically bacteria. For example and without limitation the bacterium *Bacillus subtilis* (*B.subtilis*) is known to produce and secrete a number of proteins. One family of these proteins, α-amylases, is of industrial importance and therefore the harvesting of this secreted protein is an activity currently undertaken by industry. However, the yield of some α-amylases is significantly reduced by protein degradation during an/or following passage through the cell membrane.

It therefore follows that there is a need to provide a protein expression system which enhances the production of native and/or heterologous and/or recombinant protein and more specifically effectively enhances the secretion of protein from the cell.

The expression and secretion of heterologous and/or recombinant protein (i.e. proteins that are not native to that particular bacteria) typically involves transformation of a bacterial cell with heterologous DNA with a view to manufacturing or producing heterologous and/or recombinant proteins.

Microorganisms such as *Escherichia coli* (bacteria), *Saccharomyces cerevisiae, Aspergillus nidulans* and *Neurospora crassa* (fungi) have been used in this fashion. The expression of heterologous protein in primitive eukaryotes also allows some desirable eukaryotic post-translational modifications to occur in heterologous and/or recombinant proteins leading to an increase in the stability of the expressed proteins and subsequent improvement in yield. More recently the use of mammalian and insect cells have been developed to facilitate the expression of eukaryotic proteins that for various reasons cannot be expressed in a prokaryotic host cell.

However, the cost effectiveness of producing heterologous and/or recombinant protein still remains the major advantage offered by genetically engineered prokaryotic expression systems and indeed significant advances have been made in the development of genetically engineered *E.coli* strains that increase the yield of specific proteins. The development of these bacterial strains has also been married with an ever increasing development of more efficient vectors adapted to optimise the expression of recombinant protein. These vectors contain promoter elements that are genetically engineered to create hybrid promoters that can be switched on or off with ease.

However, there are three major disadvantages when using *E.coli* as a means of expressing heterologous and/or recombinant protein. Firstly, the high levels of expression lead to a precipitation of recombinant protein in the bacterial cytoplasm as "inclusion bodies". This feature was thought to be advantageous as it can provide a simple means of separating the insoluble recombinant protein from the soluble endogenous *E.coli* protein. However, in reality this advantage is not a general feature of the system as in many cases proteins remain an insoluble precipitate that can only be released into solution by using strong chaotropic agents. This presents a major problem if the protein in question is particularly labile and therefore loses biochemical or biological activity upon denaturation. Secondly, the expression of foreign protein in *E.coli* leads to rapid degradation of these proteins via an efficient proteolytic system. Thirdly, it is known by those skilled in the art that *E.coli* usually does not naturally secrete protein into its surrounding environment. Therefore, the purification of native, heterologous or recombinant protein has the major disadvantage that the desired protein has to be purified from endogenous *E.coli* protein.

*E.coli* strains have been engineered to allow the expression of recombinant proteins that would ordinarily be difficult to express in traditional laboratory strains of *E.coli*. However, these engineered *E.coli* strains are invariably not as biologically disabled as traditional laboratory strains of *E.coli* and as a consequence require containment levels that are higher than would normally be required.

The identification of alternative prokaryotic host cells and the development of means that facilitate the production of soluble, intact and biologically active protein is obviously desirable. However, notably the number of potential prokaryotic host cells is huge.

With a view to producing a novel protein and expression system we have chosen to genetically engineer, as our example, Bacillus, ideally *B.subtilis*, in order to provide an expression system that overcomes the problems of yield associated with prior art systems. We have focussed our attention on providing a Bacillus expression system that produces and ideally secretes protein(s) into the culture medium because this system enables an initial purification of the manufactured protein due to the absence of contaminating endogenous bacterial protein(s) and other macromolecules.

The biochemical composition of the *B.subtilis* cell wall is quite different from that of *E.coli*. The cell walls of *E.coli* and *B.subtilis* contain a framework that is composed of peptidoglycan, a complex of polysaccharide chains covalently cross-linked by peptide chains. This forms a semi-rigid structure that confers physical protection to the cell since the bacteria have a high internal osmotic pressure and can be exposed to variations in external osmolarity. In Gram-positive bacteria, such as the members of the genus Bacillus, the peptidoglycan framework may represent as little as 50% of the cell wall complex and these bacteria are characterised by having a cell wall that is rich in accessory polymers such as wall teichoic acids. In addition, teichoic acids may be attached to the outside of the cytoplasmic membrane in the form of lipoteichoic acids or membrane anchored wall teichoic acids.

Teichoic acids are simple polymers of alditol phosphate molecules linked to each other by phosphodiester bridges. The free hydroxyl groups of the alditol phosphate backbone may be occupied by alanine or sugar residues. The alanylation of teichoic acids has a major effect of neutralising the negative charge conferred by adjacent phosphate residues, thereby reducing the overall negative charge of the cell wall.

The cell wall therefore provides, amongst other things, protection to the cell membrane to prevent rupture. The peptidoglycan framework represents upto approximately 50% of the cell wall mass. The remaining wall material consists of components which differ significantly between Gram negative (*E.coli*) and Gram positive (*B.subtilis*) bacteria. *B.subtilis*, and many other Gram positive bacteria, is characterised by having a cell wall that is rich in the accessory molecule teichoic acid.

The alanylation of teichoic acids is controlled by the D-alanyl-lipoteichoic acid (dlt) operon, a cluster of five genes encoding proteins necessary for the alanylation of teichoic acid. The genes are termed dltA, dltB, dltC, dltD and dltE. With the exception of dltE, each of these genes have known functions, Perego et.al 1995, please see FIG. 1.

The partial or complete deletion of any individual member of the dlt operon, with the exception of the dltE, completely inhibits the alanylation of teichoic acid. However, there is no obvious phenotypic effect of deleting one or more of the dltA–D genes other than the inhibition of alanylation and consequential changes in the overall surface charge. Cell division and growth are apparently unaffected in B.subtilis.

An unrelated gene, prsA, encodes a cell membrane located chaperone like molecule. The protein is involved in the folding of secreted proteins on the extracytoplasmic side of the cytoplasmic membrane (Kontinen et.al. 1991; Jacobs et.al 1993). Sequence homology with several peptidyl-prolyl-isomerases suggests that the PrsA protein is involved in the isomerisation of proline residues between cis and trans isomers in secreted proteins. A number of mutations have been identified and are relatively easy to determine by the diminished ability of prsA mutants to secrete α-amylase. An example of one such mutation is prsA3, Kontinen and Sarvas, 1993. Interestingly although mutants possessing a mutation in prsA show a decrease in the secretion of α-amylase and exoprotease, some secreted proteins, for example penicillinase, are unaffected. This suggests that PrsA is selectively involved in the secretion of proteins and that this selection may be determined by the number/position of proline residues or nature of its nearest neighbours in secreted proteins.

In an attempt to identify second site suppressors of prsA3 we have randomly mutagenised B.subtilis with the mini-transposon, Tn-10. This transposon randomly integrates into bacterial DNA and, as long as an essential gene is not disrupted, the Tn10 mutants are viable.

We have taken a B.subtilis strain carrying the prsA3 mutation and identified Tn10 integration mutants that show enhanced secretion of α-amylase into the culture medium. One such mutant, designated IH7231 was further analysed by DNA sequencing of the flanking regions of rescued Tn10 DNA to identify the site of integration. After sequence comparisons of the rescued DNA with the published B.subtilis genomic sequence we suprisingly found the rescued sequence to be homologous to the dltD gene of the dlt operon, Perego et.al. 1995.

The published prior art does not indicate an involvement of the dlt operon in the secretion of proteins from B.subtilis. Indeed the only apparent phenotypic change in B.subtilis cells disrupted for any of the dltA–D genes is the failure of the cell to add D-alanine to wall or lipo-teichoic acids. It is therefore both suprising and intriguing that the disruption of a dlt gene should have this phenotype.

It is therefore an object of this invention to develop a means of expressing recombinant protein in a prokaryotic expression system that allows the production of proteins and/or polypeptides in a biologically active form and at high concentration.

It is further object of the invention to develop a prokaryotic expression system that enables the secretion of native, heterologous or recombinant protein into culture medium to facilitate the purification of proteins and/or polypeptides that retains biological activity.

According to a first aspect of the invention there is provided a bacterial strain whose genome includes the dlt operon wherein the operon has been altered by substitution and/or deletion and/or insertion and/or mutation so that either production of at least part of at least one product(s) encoded by said dlt operon is prevented or at least part of at least one gene product is non-functional to the extent that the use of the strain to produce native, heterologous or recombinant protein is facilitated.

Reference hereto the term bacterial strain includes reference to any bacterial strain but ideally a Gram-positive bacterial strain and, more ideally, but not obligatory, a bacterial strain of the genus Bacillus.

It will be apparent to those skilled in the art that where heterologous and/or recombinant protein is to be produced the said bacterial strain will be transformed so as to include DNA encoding at least one selected heterologous and/or recombinant protein.

Figure 1:
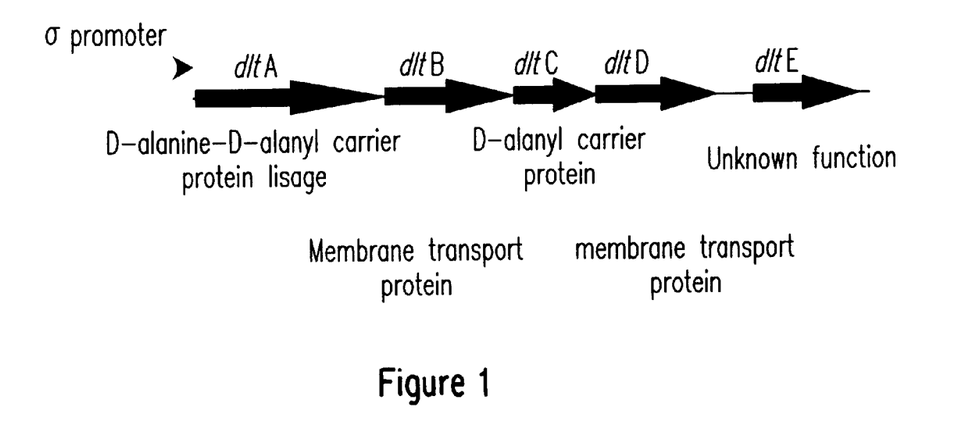
FIG. 1 is a graphical representation of the dlt operon of B.subtilis.

It will also be apparent to one skilled in the art that said alteration may be to at least one of the dlt A–E genes as represented in FIG. 1. So that said alteration ideally leads to a failure of said strain to add D-alanine to teichoic acid.

In a further preferred embodiment of the invention said alteration is to at least part of the dlt A–E genes.

In yet a further preferred embodiment of the invention said alteration is to at least part of dltA and/or dltB and/or dltC and/or dltD and/or dltE, preferably dltB but ideally dltD.

It will be apparent that means to effect said alteration to the dlt operon are well known in the art. For example, and not by way of limitation, the insertion of genetic material into the dlt operon may be undertaken by transposon integration. Additionally or alternatively, the operon may be altered to provide for deletion of at least part of at least one gene located in the dlt operon by homologous recombination with at least one suitably designed vector and/or the replacing of at least part of at least one gene located in the dlt operon with homologous DNA carrying, for example, a translation termination codon thus preventing synthesis of a functional protein. Additionally or alternatively, the operon may be altered by base substitution and/or mutation by random or site-directed mutagenesis.

In yet a further preferred embodiment of the invention said dlt operon is altered by way of alteration of an expression control sequence, ideally a promoter, such that the promoter is made responsive to a specific signal, for example, the operon may be placed under the control of an inducible promoter such that expression of the operon encoded gene products may be selectively controlled.

It is well known in the art that means to place the aforedescribed genes under the control of regulatable promoters exist and include those means described for placing the dlt operon under regulatable expression.

The dlt operon is controlled by a single promoter element regulated by the transcription factor (sigma D or $\sigma^D$), therefore the above embodiment of the invention may comprise replacement of sigma D or $\sigma^D$ with, for example, and not by way. of limitation, an IPTG inducible promoter. By placing the dlt operon under the control of an IPTG inducible promoter the expression of proteins encoded by the dlt operon can simply be induced by addition of IPTG.

Alternatively the expression of the dlt operon may be repressed by, for example and not by way of limitation, incorporation of a tetracycline responsive element. The tetracycline responsive element binds the TET repressor protein to prevent transcription from a promoter containing the responsive element. Therefore a bacterial strain according to the invention could be further genetically engineered to contain a gene expressing the TET repressor and a dlt operon containing the TET responsive element.

Methods to manipulate bacterial promoters in the aforedescribed manner are well known in the art.

In an alternative embodiment of the invention said alteration according to the invention involves manipulation of the native promoter element in a manner that results in the provision of a non-functional promoter element incapable of initiating transcription at the dlt operon.

In an alternative embodiment of the invention said alteration of an expression control sequence is an alteration to at least one mRNA stabilising sequence element located in non-coding regions of the dlt operon. More ideally still, said non-coding regions are located in the 5' or 3' non-translated regions of mRNA molecules encoded by the dlt operon.

It is well known in the art that the stability of bacterial mRNA is controlled to a greater extent by sequences located at the 3' end of mRNA which interact with proteins to either stabilise or de-stabilise mRNA molecules. The selective deletion, substitution, insertion or mutation of the sequences may de-stabilise MRNA molecules derived from the dlt operon but in any event results in decreasing and/or inhibition in the expression of dlt encoded proteins.

In yet a further preferred embodiment of the invention said alteration of an expression control sequence is to 5' translation control sequences of mRNAs encoded by the dlt operon.

Translation control sequences are well known in the art and include, by example and not by way of limitation, Shine Dalgarno sequence motifs found near the translation start codon in many prokaryotic mRNA's.

In a third aspect of the invention there is provided a method for producing a desired native, herlogous or recombinant protein and/or polypeptide, wherein bacteria, as aforedescribed, is used for the production of the protein and/or polypeptide by;

i optionally, transforming a bacterial strain according to the invention with a suitable vector genetically engineered to facilitate expression of said polypeptide;

ii culturing said bacterial strain under conditions conducive to the production of said polypeptide; and iii recovering and purifying the said polypeptide from said bacterial strain and/or growth medium.

The introduction of a vector into a bacterial strain according to the invention may be by any method known in the art, such as conventional transformation methods, electroporation, conjugation or protoplast transformation. The expression construct may be a plasmid or any other vector suitable for the specific method used for introducing said expression construct into a bacterial cell.

In essence the invention provides a bacterial strain, ideally a B.subtilis strain, that has been mutated to provide a bacterial strain that is facilitated in the secretion of native, heterologous or recombinant protein into surrounding growth medium.

An embodiment of the invention will now be described by way of example only with reference to the following figures wherein:

BRIEF DESCRIPTION OF THE DRAWINGS

FIGS. 5a–5b.

MATERIALS AND METHODS

TABLE 1

Bacterial strains and plasmids

| B. subeilis strain | Genotype/Phenotype |
|---|---|
| IH6531 | glyB133 hisA1 trpC2, pKTH10 |
| IH7144 | glyB133 hisA1 prsA3, pKTH10 |
| IH7200 | glyB133 hisA1 prsA3, pKTh10, pHV1248 |
| IH7231 | glyB133 hisA1 prsA3 dltD::miniTn10, PkTh |
| IH7347 | glyB133 hisA1 trpC2, pKTH239 |
| IH7378 | glyB133 hisA1 trpC2 dltD::miniTn10, pKTH10 |
| IH7379 | glyB133 hisA1 trpC2 dltD::miniTn10, pKTH239 |
| JH642 | TrpC2 pheA1 |
| DLT71 | JH642 with prom, dltB |
| DLT72 | JH642 with dltB |
| DLT74A | JH642 with dltDE |
| DLT76 | JH642 with dlTE |
| DLT77 | JH642 with dltC |
| DN1885 | AmyE |
| DN1885 xylR::pKS402 | DN1885 with chromosomal integration of pKS402 at xylR |
| DN1885 xylR::pKS402 dltB | DN1885 dltB with chromosomal integration of pKS402 at xylR |
| DN1885 xylR::pKS405B | DN1885 with chromosomal integration of pKS405B at xylR |
| DN1885 xylR::pKS405B dltB | DN1885 dltB with chromosomal integration of pKS405B at xylR |
| DN1885 xylR::pKS408 | DN1885 with chromosomal integration of pKS408 at xylR |
| DN1885 xylR::pKS408 dltB | DN1885 dltB with chromosomal integration of pKS408 at xylR |
| Plasmids | |
| pKS402 | Ap$^r$, Km$^r$, amyLQS50.1, xylR |
| pKS405B | Ap$^r$, Km$^r$, amyLQS50.5, xylR |
| pKS408 | Ap$^r$, Km$^r$, amyL, xylR |
| pKTh10 | Km$^r$, amyQ |
| pKTh239 | Km$^r$, P$_{amyQ}$-pnl |
| pHV1248 | Em$^r$, Cm$^r$ miniTn10, ori-pE194ts |

Growth Media

B.subtilis and E.coli were maintained on antibiotic medium number 3 (Difco) solidified with 1.5% w/v agar and containing 1% w/v soluble starch. Batch cultures were grown in 2×YT broth buffered with 0.2M MES pH 6.5 which contained; tryptone (1.6% w/v), yeast extract (1.0% w/v) and NaCl (0.5% w/v). Where required antibiotics were included in the growth media at the following final concentrations: chloramphenicol 6μg/ml, ampicillin 100μg/ml and erythromycin 1μg/ml. Xylose (1% w/v) was added to induce the synthesis of α-amylase from a xylose-inducible promoter.

DNA Manipulations and Bacterial Transformation

Restriction digestion, DNA fragment purification, ligation and transformation of E.coli were carried out as described previously (Sambrook et al., 1989). Chromosomal DNA was isolated from B.subtilis using the IGi Genomic extraction kit (Immunogen International) or as described in Marmur, 1961. PCR was carried out with Taq DNA polymerase (Appligene) using B.subtilis DN1885 chromosomal DNA or plasmid pEV1248 as the template. Plasmid DNA was purified from E.coli and B.subtlis with the Tip-100 plasmid extraction kit (Qiagen). Oligonucleotide primers for PCR were synthesized using a Beckman Oligo 1000. *B.subtilis* was grown to competence and transformed with integrative plasmids.

α-Amylase Assay

The quantity of secreted α-amylase was quantified using the Phadebas α-amylase assay kit (Kabi Pharmacia). The cells from culture samples were pelleted by microcentrifugation and the α-amylase activity in the supernatant determined as described by the manufacturer.

Origin of α-Amylase. AmyLQS50.5. AmyLQS50.1. AmyL, AmyQ and Pneumolysin

*B.subtilis* strains used in this study were transformed with expression vectors encoding polypeptides which are secreted through the *B.subtilis* cell wall into the extracellular medium. The construction of AmyLQS50.1 and AmyLQS50.5 is described in Dr Keith Stephenson's PhD thesis (1996) entitled "Construction and Use of Chimeric α-Amylase to Study Protein Secretion in *Bacillus subtilis*. AmyLQS50.5 is a chimeric α-amylase and the construction is described in "Secretion of Chimeric α-Amylase from *B.subtilis*"; AmyL is derived from *B.licheniformis*; AmyQ is derived from *B. amyloliquefaciens*. Pneumolysin is derived from *Streptococcus pneumoniae*.

Generation of a *B.subtilis* Strain Disrupted for dltB

The dltB mutation was generated in DN1885 xylR::pKS405B, DN1885 xylR::pKS402 or DN1885 xylR-::pKS408 (AmyLQS50.5, AmyLQS50.1 and AmyL, respectively ) by transforming DNA from JH642::pDLT72 (Perego et al 1995 J Biol Chem 270: 15598–15606). A fragment of JH642::pDLT72 DNA with insertionally inactivated dltB integrated into the chromosome via a double cross-over event and this is selected for on nutrient agar plates containing erythromycin.

Random Mutagenesis With Mini Tn 10 Transposon

Tn mutagenesis was performed as described in (Petit et al., 1990) with the strain IH7200. IH7200 is a prsA3 mutant, which harbors the plasmid pKTH10 (Palva, 1982) expressing AmyQ and the plasmid pHV1248 carrying a temperature sensitive replicon and the mini-Tn10 transposon (Petit et al., 1990). Bacteria of the strain IH7200 were grown in 10 ml of L-broth supplemented with kanamycin (10 μg/ml), erythromycin (1 μg/ml) and chloramphenicol (5 μg/ml) up to mid-exponential phase of growth (50 Klett units) at 30° C. and then shifted to 51° C. for 2.5 hours. Samples were then plated on L-plates containing 9% soluble starch, kanamycin and chloramphenicol (above concentrations), followed by incubation at 51° C. over night. Tn mutants with increased secretion of AmyQ were detected from a larger halo around colonies. A strain identified in this screen was IH7231.

Identification of Tn 10 Inactivated Gene in IH7231

The gene inactivated in IH7231 was identified by cloning a fragment of its chromosomal DNA containing the Tn10 transposon into the bacteriophage vector, Lambda GEM11 (Promega). Cloning in the lambda vector was performed according to the manufactures instructions. Plaques containing the transposon were identified by their ability to hybridise to a digoxigenin-labeled probe of the cat gene of pHV1248. DNA was isolated from a Lambda clone isolate from such a positively hybridising plaque and the DNA flanking the TN10 insert was sequenced. Comparison of the obtained sequence with the sequence of the whole genome of *B. subtilis* revealed that the gene interrupted by the transposon was dltD, the fourth gene in the dlt operon (Perego et al., 1995) responsible for the D-alanylation of lipo- and wall teichoic acids. The product of the dltD gene encodes a protein which probably catalyses the transfer of D-alanine to the lipo- and wall teichoic acids. Inactivation of the dltD gene by insertion with a derivative of the integrative plasmid pMUTIN containing part of the dltD gene, or inactivation of the second gene in the operon, dltB, with integration plasmid pDLT72 (Perego et al 1995), produced the same phenotype as that of IH7231 as determined by the halo assay or assay of α-amylase activity in culture medium. We have confirmed that the cell walls isolated from the IH6531 dltD::miniTn10 (IH7378), IH7231 and DN1885::pDLT72-derivatives encoding AmyL or AmyLQS50 contain no detectable alanine.

D-Alanine Content of Cell Walls of dltB and dltD Deletion Strains

The alanine content of the cell walls of the dltB and dltD mutants was determined according to IC Hancock and IR Poxton (1988) , Bacterial CellSurface Techniques, John Wiley and Sons, Chichester. The method involves preparing cell walls by boiling in buffered SDS (sodium dodecyl sulphate, pH6.0), hydrolysing the alanine ester linkages with 0.1M sodium pyrophosphate pH 8.3 and then assaying released alanine with the following solutions A–E mixed in the ratio 40:20:10:5:1

A) 0.1M 0.1M sodiun pyrophosphate pH 8.3

B) 0.2 mg/ml FAD in 0.1M sodiun pyrophosphate pH 8.3

C) Horseradish peroxidase (200 U/mg) at 50 micrograms per milliliter in water

D) Dianisidine sulphate, 5 mg/ml in water

E) D-amino acid oxidase (15 U/mg) at 5 micrograms per milliliter in water. The reaction is stopped by the addition of 0.1% SDS and absorbance measured at 460 nm. The results of these assays are presented in table 1

Results

We have confirmed the beneficial activity of dlt operon knockouts on the production of proteins by measuring the production of 3 commercially important proteins, namely AmyL, AmyQ and Streptococcal pneumolysin.

Increased α-Amylase Secretion in dltD and dltB Gene Disruptans

Figure 2:
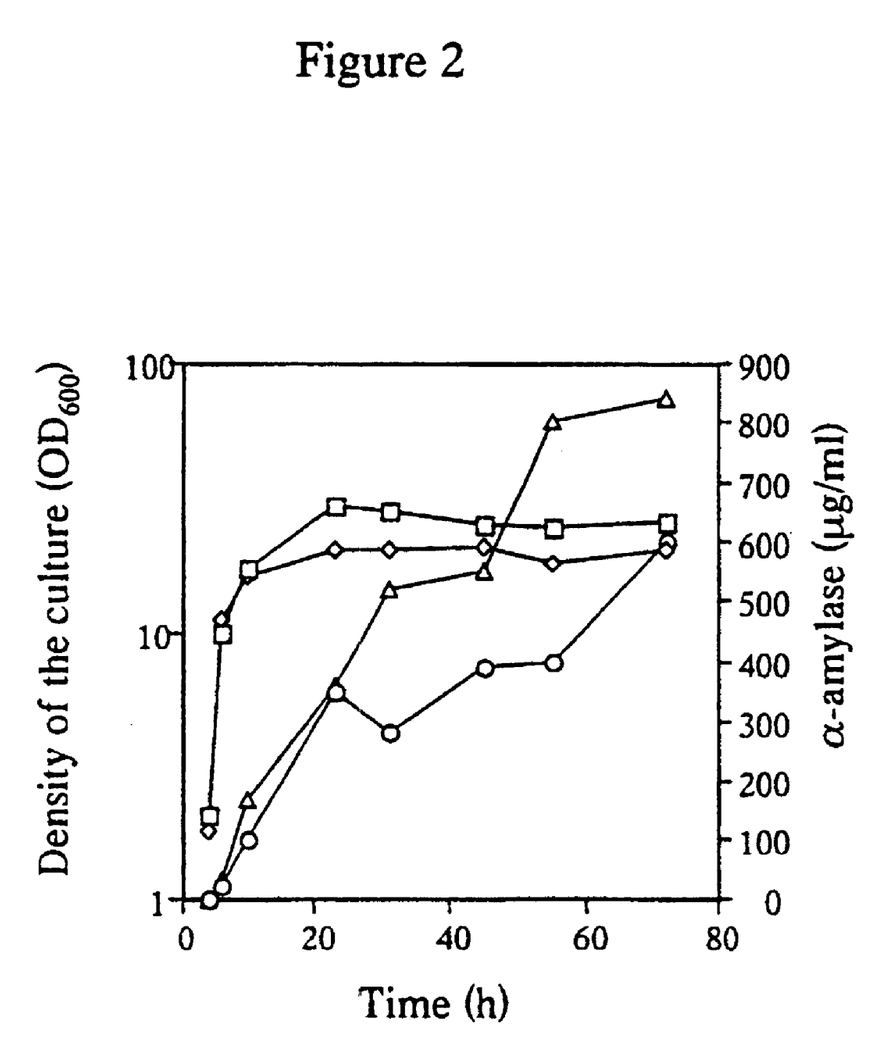
FIG. 2 represents the accumulation of heterologous and/or recombinant α-amylase (Amy Q) in culture media of a B.subtilis strain disrupted for dltD.

In the case of AmyQ, wild type (IH6531) and dltD::miniTn10 (IH7378) strains harbouring pKTH10 were cultured for 72 hours in double-strength L-broth containing starch and 100 mM bis-tris propane, pH 6.5 at 37° C. in shake flasks. α-Amylase was assayed in the culture supernatant using the Phadebas assay kit (Pharmacia). The levels of α-amylase were similar in exponential phase and early stationary phase, however, as stationary phase was prolonged, increasingly higher amounts of α-amylase were produced by the strain with the dltD mutation. After 72 hour of growth, the amount of α-amylase in the dltD mutant was about 50% higher than in the wild type strain, see FIG. 2.

Figure 3:
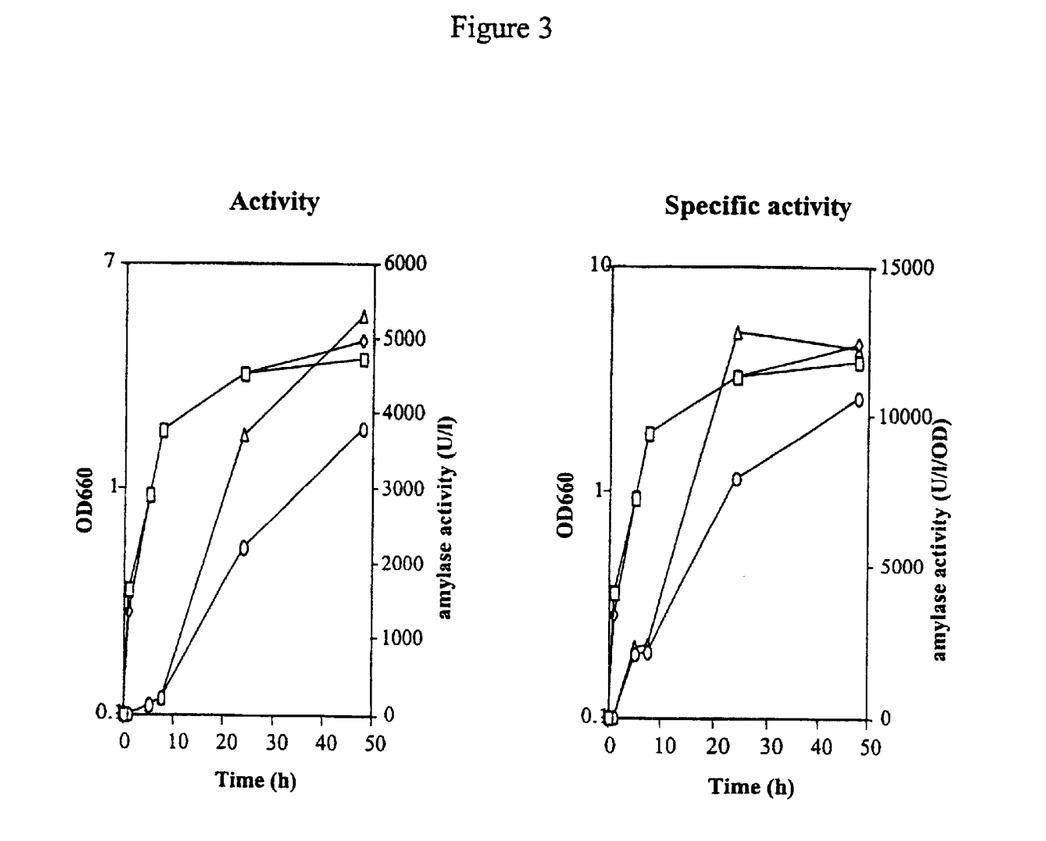
FIG. 3 represents the accumulation heterologous and/or recombinant α-amylase (Amy L) in culture media of a B.subtilis strain disrupted for dltB.

In a complementary experiment, production of AmyL was monitored in DN1885 xylR::pKS408 with or without the dltB inactivated with pDLT72. The strains were grown at 37° C. with shaking in 2×YT containing 0.2M MES buffer at pH 6.5. α-Amylase activity was again measured in the culture medium and the dltB mutant showed an increased in α-amylase production, of about 40% compared to the wild type strain, FIG. 3. In the case of wild type and dltB strains encoding a derivative of AmyL, namely AmyLQS50.1, the amount of amylase produced was approximately double.

Figure 5A:
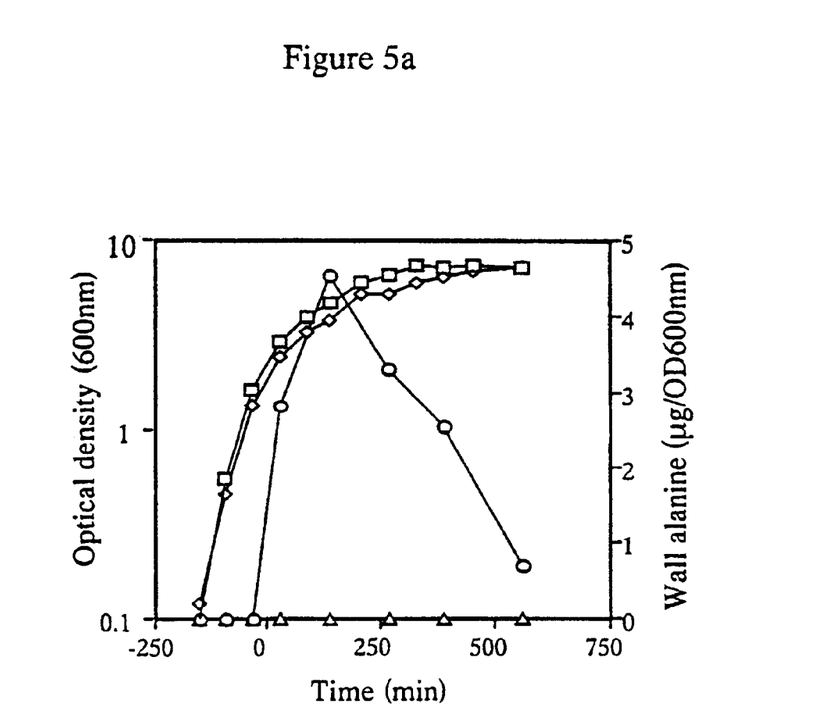
FIG. 5a represents the alanine content of B.subtilis cell walls of wild type and a strain disrupted for the dltB gene.
Figure 5B:
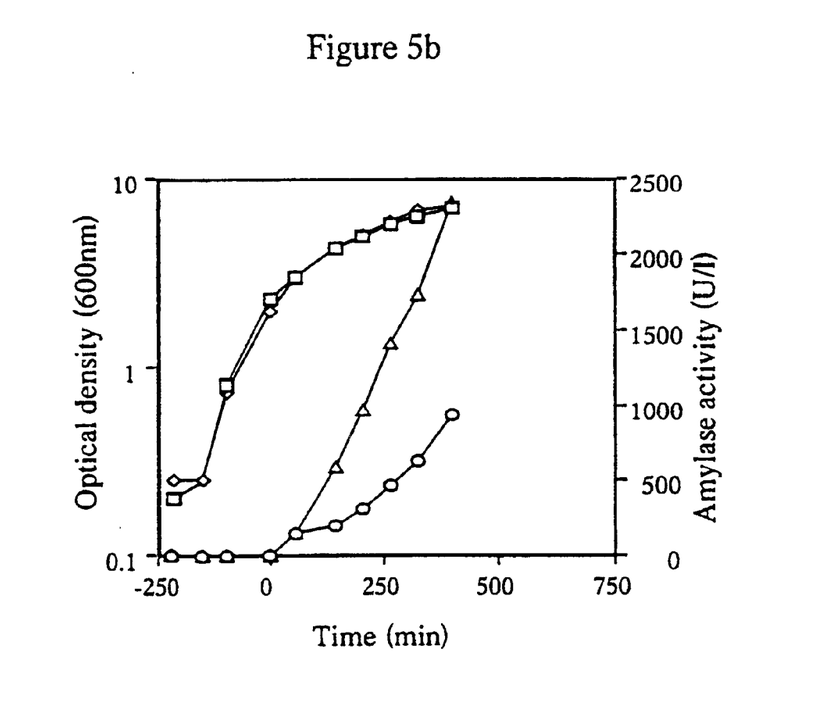
FIG. 5b represents the accumulation of heterologous and/or recombinant α-amylase (AmyL) in culture media of wild type B.subtilis and a strain disrupted for the dltB gene.

A comparison of the alanine content of cell walls of *B.subtilis* wild type (DN1885 xylR:: pKS405b) and the dlt B gene deletion DN1885 xylR:: pKS405B dlt shows that although alanine content is negligible in the mutant strain, cell division is unaffected, please see FIG. 5a. The production of AmyL is approximately 2-fold enhanced in the deletion strain, see FIG. 5b.

Figure 6A:
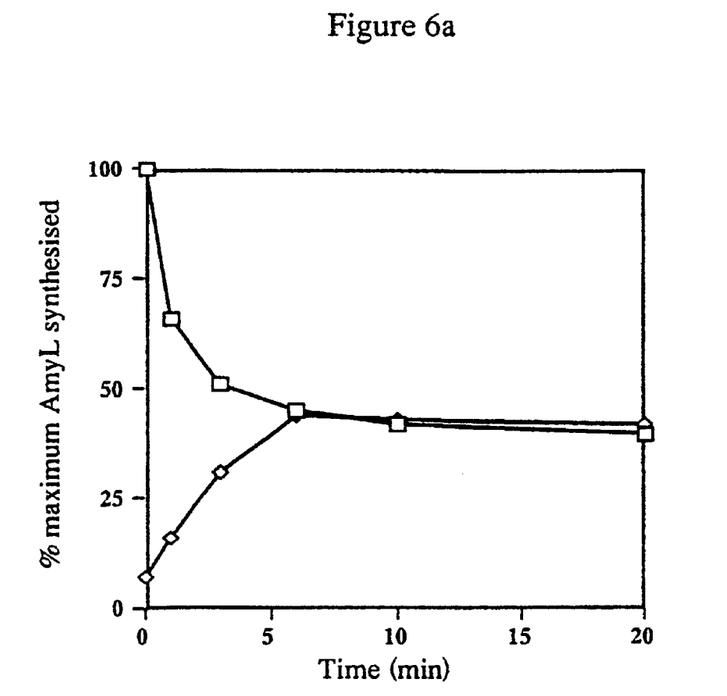
FIGS. 6a and 6b represents a comparison of the synthesis and release of heterologous and/or recombinant α-amylase (AmyL) from wild type B.subtilis and a strain disrupted for the dlt B gene.
Figure 6B:
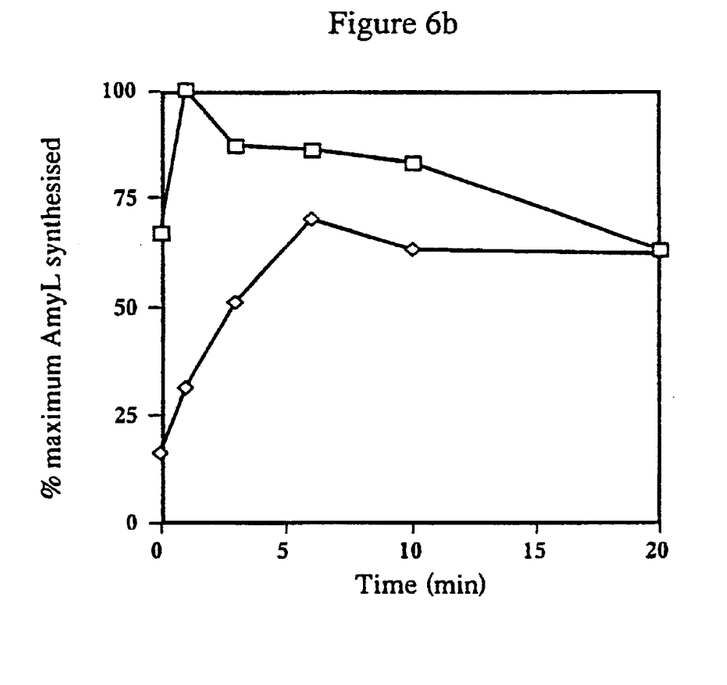

The amount and cellular distribution of AmyL synthesized by wild type B. subtilis and the dlt B deletion strain was compared, see FIGS. 6a and 6b. The mutant strain shows both enhanced total synthesis (cell associated and released) and release of AmyL into culture medium, FIG. 6b.

Increased Pneumolysin Secretion in dlt D Gene Disruptants

Figure 4:
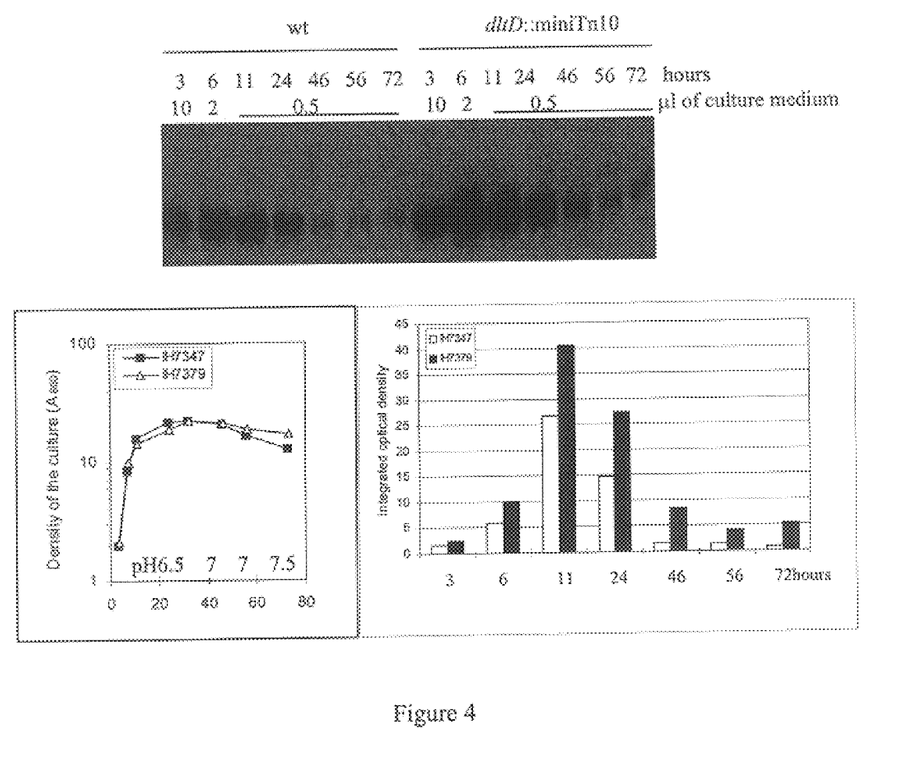
FIG. 4 represents the accumulation of heterologous and/or recombinant pneumolysin in culture media of a B.subtilis strain disrupted for dltD.

In the case of streptococcal pneumolysin, strains IH7347 (wild type) and IH7379 (dltD::Tn10) both harboured pKTH239, a derivative of pUB110 encoding the structural gene of pneumolysin fused to the amyQ promoter and signal sequence. Cells were grown for 72 hours in double-strength L-broth containing starch and 100 mM bis-tris propane, pH 6.5 at 37° C. in shake flasks. Sample of culture medium were removed at different times during growth and, after boiling in 1% SDS, were subjected to SDS-PAGE in 12% gels. After electrophoresis, the samples were immunoblotted and polypeptides cross-reacting with pneumolysin antiserum was detected with an enhanced chemoluminesence system (Amersham), FIG. 4. The amount of pneumolysin was about 50% higher in the dltD deletion strain at all stages of growth.

Discussion

We have used a strain of B. subtilis that is severely impaired for the secretion of α-amylase to identify an operon, the dlt operon, that influences the secretion of proteins from B. subtilis and we have subsequently verified the involvement of the dlt operon by placing it under the control of an IPTG inducible promoter to regulate the production of dlt encoded products. The observation that the products of dlt operon affected the secretion of α-amylase in a negative manner was unexpected since their role in the alanylation of wall and lipo-teichoic acids was already established.

The role of dlt encoded products in alanylation of teichoic acids was confirmed by the biochemical analysis of alanine content in the cell walls of various B.subtilis strains carrying lesions in the dit operon, please see Table 2. A comparison of the doubling time for wild-type and dlt mutant strains shows that the strains carrying lesions in the dlt operon do not appear to be compromised in growth, at least under these growth conditions. The only apparent phenotype of this class of mutation is a reduction in alanylation of teichoic acids and an increase in secretion of selected heterologous/recombinant protein.

Although secretion of α-amylase is affected in exponential phase, the influence of lesions in the dlt operon is most pronounced in stationary phase. This is significant because the stationary phase is the most productive phase in commercial fermentations.

The initial experiments showed that a dltD::Tn10 mutant was able to produce more of the B. amyloliquefaciens α-amylase, the involvement of this gene was confirmed by use of two other types of insertion mutant. We have also shown that mutations in the dltB gene affect the synthesis of another α-amylase, that from B. licheniformis, in a similar manner. In both cases we confirmed that the cell walls lacked the D-alanine substituents that were present in the wild type.

Finally, we have also shown that strains with the dlt-D::Tn10 mutation were able to produce increased amounts of the pneumolysin from Streptococcus pneumoniae, another example of a commercially important enzyme which is not related to α-amylase and is derived from a genus other than Bacillus .

The mechanism by which inactivation of the dlt operon affects secretion is not known. It could influence exoproteins directly, for example by increasing their rate of folding as they emerge on the trans side of the membrane from the secretory translocase. Alternatively, the lack of alanylation may reduce the activity of wall or membrane protease, modulate the concentration of metal cofactors or increase the wall porosity of the cell wall.

REFERENCES

Jacobs, M., Anderson, J. B., Kontinen, V. P. and Sarvas, M. (1993) Mol.Microbiology, 8: 957–966.
Kontinen, V. P., Saris, P. and Sarvas, M. (1991) Mol.Microbiology, 5:1273–128.3
Kontinen, V. P. and Sarvas, M. (1993) Mol.Microbiology, 8: 727–737.
Marmur, J. (1961) J. Mol. Biol. 3: 208–218.
Pavla, I (1982) Gene. 15: 43–51.
Petit, M. A., Bruand, C., Janniere, L. and Ehrlich, D. S. (1990) J.Bacteriol., 172: 6736–6740.
Perego, M., Glaser, P., Minutello, A., Straunch, M. A., Leopold, K. and Fischer, W. (1995) J.Biol.Chem, 270: 15598–15606.

TABLE 2

D-alanine content of wall teichoic acids extracted from various strains of B. subdlis

| Strain | D-alanine content 7.5 hours growth | D-alanine content 24 hours growth | dlt lesion |
|---|---|---|---|
| JH642 | no data | 5.7 | none |
| DLT71 | no data | none detected | prom, dltAB |
| DLT72 | no data | none detected | dltB |
| DLT74A | no data | none detected | dltDE |
| DLT76 | no data | 5.65 | dltE |
| DLT77 | no data | none detected | dltC |
| DN1885 xylR::pKS402 | 13.2 | 5.89 | none |
| DN1885 xylR::pKS402 dltB | none detected | none detected | dltB |
| DN1885 xylR::pKS405B | 8.84 | 4.58 | none |
| DN1885 xylR::pKS405B dltB | none detected | none detected | dltB |
| DN1885 xylR::pKS408 | 19.62 | 11.84 | none |
| DN1885 xylR::pKS408 dltB | none detected | none detected | dltB |
| IH 6531 | 14.83 | no data | none |
| IH 6531 dltD (IH7378) | none detected | no data | dltD |
| IH 7144 | 18.25 | no data | none |
| IH 7144 dltD (1H7231) | none detected | no data | dltD |

We claim:

1. A method for producing a native, heterologous or recombinant secreted polypeptide, wherein said method comprises:
   i) providing a Gram positive bacterial strain which expresses the native, heterologous or recombinant secreted polypeptide and the genome of which includes the dlt operon which has been altered by substitution, deletion, insertion and/or mutation, so that at least part of at least one gene product of the dlt operon is not expressed or is rendered non-functional;
   ii) incubating said bacterial strain under conditions conducive to the production of said polypeptide; and
   iii) recovering and purifying said polypeptide from said bacterial strain and/or growth medium.

2. A method according to claim 1, wherein said bacterial strain is transformed with an expression vector comprising a gene encoding the polypeptide.

3. A method according to claim 1, wherein said bacterial strain belongs to the genus Bacillus spp.

4. A method according to claim 3, wherein said bacterial strain is selected from the group consisting of B.subtilis, B.licheniformis and B.amyloliquefaciens.

5. A method according to claim 1, wherein at least part of dlt A gene and/or dlt B gene and/or dlt C gene and/or dlt D gene and/or dlt E gene is altered.

6. A method according to claim 5, wherein at least part of the dlt D gene is altered.

7. A method according to claim 5, wherein at least part of the dlt B gene is altered.

8. A method according to claim 1 wherein said dlt operon is altered by way of alteration of an expression control sequence.

9. A method according to claim 8 wherein said dlt operon is altered by way of alteration of a promoter control sequence.

10. A method according to claim 9 wherein said promoter control sequence is altered by incorporation of an inducible promoter sequence element.

11. A method according to claim 9 wherein said promoter control sequence is altered by the incorporation of a repressor promoter sequence element.

12. A method according to claim 9 wherein said promoter control sequence is altered so as to provide a non-functional promoter control sequence.

13. A method according to claim 8 wherein said alteration of an expression control sequence is an alteration to at least one mRNA stabilising sequence element located in a non-coding region of the dlt operon.

14. A method according to claim 13, wherein said non-coding region is located in the 5' untranslated region of an mRNA molecule encoded by the dlt operon.

15. A method according to claim 14 wherein said alteration of an expression control sequence is to the 5' translation control sequence of an mRNA encoded by the dlt operon.

16. A method according to claim 1 wherein the polypeptide is an α amylase.

17. A method according to claim 13, wherein said non-coding region is located in the 3' untranslated region of an mRNA molecule encoded by the dlt operon.

18. A method according to claim 13, wherein alterations are effected in non-coding regions located in the 5' and 3' untranslated regions of an mRNA molecule encoded by the dlt operon.

\* \* \* \* \*